United States Patent
DiCaprio

(10) Patent No.: US 7,291,167 B2
(45) Date of Patent: Nov. 6, 2007

(54) STENT HAVING RADIOPAQUE MARKERS AND METHOD OF FABRICATING THE SAME

(75) Inventor: Fernando DiCaprio, Mendota Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 594 days.

(21) Appl. No.: 10/321,989

(22) Filed: Dec. 17, 2002

(65) Prior Publication Data

US 2003/0121148 A1    Jul. 3, 2003

Related U.S. Application Data

(62) Division of application No. 09/697,634, filed on Oct. 26, 2000, now abandoned.

(51) Int. Cl.
    *A61F 2/06* (2006.01)
(52) U.S. Cl. .................. 623/1.34; 623/900
(58) Field of Classification Search .............. 623/1.34, 623/1.44, 1.45, 1.46, 900; 427/2.24, 2.25, 427/2.3; 428/374
    See application file for complete search history.

(56) References Cited

U.S. PATENT DOCUMENTS

| | | | |
|---|---|---|---|
| 4,699,611 A | 10/1987 | Bowden | 604/51 |
| 5,201,901 A | 4/1993 | Harada et al. | |
| 5,674,276 A | 10/1997 | Andersen et al. | 623/1 |
| 5,725,570 A | 3/1998 | Heath | 623/1 |
| 5,725,572 A | 3/1998 | Lam et al. | 623/1 |
| 5,741,327 A | 4/1998 | Frantzen | 623/1 |
| 5,807,404 A | 9/1998 | Richter | 623/1 |
| 5,836,964 A | 11/1998 | Richter et al. | 606/194 |
| 5,836,969 A | 11/1998 | Kim et al. | 606/200 |
| 5,913,896 A | 6/1999 | Boyle et al. | 623/1 |
| 5,922,005 A | 7/1999 | Richter et al. | 606/192 |
| 5,938,682 A | 8/1999 | Hojeibane et al. | 606/198 |
| 5,980,564 A | 11/1999 | Stinson | 623/1 |
| 5,984,963 A | 11/1999 | Ryan et al. | 623/12 |
| 6,022,374 A | 2/2000 | Imran | 623/1 |
| 6,059,810 A | 5/2000 | Brown et al. | 606/198 |
| 6,081,104 A | 6/2000 | Kern | 323/268 |
| 6,083,257 A | 7/2000 | Taylor et al. | 623/1 |
| 6,102,938 A | 8/2000 | Evans et al. | 623/1 |
| 6,117,165 A | 9/2000 | Becker | 623/1 |
| 6,261,319 B1 | 7/2001 | Kveen et al. | 623/1.15 |
| 6,471,721 B1 * | 10/2002 | Dang | 623/1.34 |
| 6,508,832 B1 * | 1/2003 | Jalisi et al. | 623/1.15 |
| 6,623,520 B2 * | 9/2003 | Jalisi | 623/1.15 |

FOREIGN PATENT DOCUMENTS

WO    93/19804    10/1993
WO    97/33534    9/1997

OTHER PUBLICATIONS

Schetsky, L. "Shape Memory Alloys" *Encyclopedia of Chemical Technology*, 3rd Ed. vol. 20, p. 726-736.
"A Source Manual for Information on Nitinol and NiTi," 1st revision by David Goldstein, Research and Technology Department, Feb. 1, 1980, Naval Surface Weapons Center, Dalgreen, VA. 22448.
U.S. Appl. No. 08/511076, filed Aug. 3, 1995, inventor Brown et al.
Schetsky, L. McDonald, "Shape-Memory Alloys" *Scientific American*, 241(5):74-82 (Nov. 1979).

* cited by examiner

*Primary Examiner*—William H. Matthews
(74) *Attorney, Agent, or Firm*—Vidas, Arrett & Steinkraus, P.A.

(57) ABSTRACT

The present invention relates to an intraluminal medical device formed of a first base material and having a second material inlaid in the base material wherein at least one of said first material and said second material is more radiopaque than the other. The second material may be inlaid in the first either by swaging, rolling, or by coextruding the two materials. The second radiopaque material forms a substantially smooth surface with the first base material.

3 Claims, 20 Drawing Sheets

STENT HAVING RADIOPAQUE MARKERS AND METHOD OF FABRICATING THE SAME

This is a division of U.S. patent application Ser. No. 09/697,634 filed Oct. 26, 2000 and now abandoned.

FIELD OF THE INVENTION

The present invention relates to an expandable intraluminal device, in particular a stent, having radiopaque markers which are inlaid in the base material of the intraluminal device for enhancing the visibility of the device when viewed through a fluoroscope or other imaging device, and to a method of making the same.

BACKGROUND OF THE INVENTION

It is known to implant medical devices such as stents, stent-grafts, vena cava filters, and so forth, into body lumens, such as arteries to reinforce, support, repair or otherwise enhance the blood flow through the lumen.

Stents are commonly used where an artery is blocked, or otherwise damaged. The stent, once in place, reinforces that portion of the artery allowing normal blood flow to occur through the artery. One type of stent that is popularly used for such purposes is a radial expandable stent. This is a tubular or cylindrical stent which can be radially expanded from a first smaller diameter to a second larger diameter. These stents are either self-expanding, or are pressure-expandable.

The stents are inserted into an artery through the use of a stent delivery device and are fed internally through the arterial pathways of the patient until the unexpanded stent is located where desired. The catheter may either be fitted with a balloon in the case of a pressure expandable stent, or with stent retaining sleeves in the case of a self-expanding device. These expandable stents have properties such that they remain expanded after the catheter has been removed.

One problem encountered in the use of radially expandable surgical stents is the difficulty in precisely determining the position of the stent both before, during and after it is implanted and expanded. Stents are typically formed of metals or metal alloys including stainless steel, shape memory alloys such as nickel-titanium alloys, or some other such alloy which in and of themselves are not readily visible using fluoroscopic imaging techniques. It is of particular importance to be able to clearly and accurately visualize the stents during the time that they are being deployed and also to be able to visualize the stents after they have been deployed, at periodic time intervals.

Attempts have been made to make such stents more radiopaque through the use of various metals such as platinum, tantalum, gold, and so forth. One such approach has been to fabricate the stent itself from such materials, such as tantalum, but the stents fabricated of radiopaque materials have been found to illuminate too brightly, resulting in haloing or obscuring of fine details such as blood vessels and other bodily structures, thus making it difficult to visualize the vessel or lesion which is being repaired.

Another approach has been to coat the stent with such materials. Several problems may be encountered using such coating methods including restriction of the expansion capabilities of an expandable stent by adding rigidity to the stent in areas designated for stent deformation, the coating can flake off of the stent if it is not securely anchored to the stent surface, and completely coating a stent can also result in haloing, a phenomenon resulting from the radiopaque material illuminating too brightly so as to obscure proper visibility of the blood vessel lesion, thereby impairing the ability to repair the lesion. Also, coatings which are too thick will significantly enlarge the thicknesses of the stent making this technique less effective on stents sized for implantation in smaller body lumens, and if the coating is too thin, insufficient radiopacity will result.

A partial or selective coating can reduce the occurrence of the above mentioned problems, but can also result in decreased efficiency in the manufacturing process. For instance, some methods of partial coating involve the added step of masking the stent in certain areas. The masking procedure is difficult to accurately perform, especially on inner surfaces of stents with small diameters.

Radiopaque markers can also be attached by mechanical or adhesive means, for instance. These methods too can have various limitations. Upon attachment to a stent, they may define a profile that is readily discernible from that of the stent, thereby comprising projections which may undesirably alter the contemplated profile of the stent. That is, they may protrude from the walls of the stent and depending upon their location upon the stent, may either project into the blood flow or into the walls of the blood vessel. Such markers can also be tedious to attach to the stent resulting in decreased efficiency in production, and they can also be difficult to attach in a precise location.

U.S. Pat. No. 5,741,327 describes the mechanical attachment of marker elements to the ends of a stent with the axial center of the marker elements being coextensive with the central axis of the stent. The marker element is configured to be radially expandable in a manner similar to the radial expansion of the stent itself. However, the marker elements are attached to the ends of the stent in positions beyond the ends of the stent. The marker elements can either be circumferentially continuous, completely circumscribing the central axis of the stent, or discontinuous with a series of disconnected marker elements secured to the ends of the stent at separate positions thereon.

There continues to be a need in the art for a new and improved radiopaque markers for use on radially expandable stents which can be utilized on stents of all different sizes, do not interfere with the expansion characteristics of the stent and provides a clear image on a fluoroscope or other medical imaging device. Furthermore, there remains a need in the art for a simple method of fabrication for such radiopaque stents that allows the fabrication using known and efficient manufacturing techniques.

SUMMARY OF THE INVENTION

The present invention relates to an intraluminal medical device having radiopacity and having a distal end, a proximal end, and a body portion. The device is comprised of a first base material and a second material inlaid in the first material, the first material and second material forming a substantially smooth surface. One of the first material or the second material is more radiopaque than the other. Preferably, the second material is more radiopaque than the first material.

The present invention further relates to a method of forming an intraluminal medical device having radiopacity comprising the steps of providing a stent preform comprised of a first material in a sheet form and inlaying a second material into the preform at specified locations, the first and second material forming a substantially smooth surface in the preform. One of the first or the second material is more radiopaque than the other. Preferably, the second material is more radiopaque than the first.

The first and second material may either be coextruded, or the second material may be inlaid into the first material by rolling, cold forging, swaging, or some other such method that results in an inlay.

The present invention further relates to a method of forming an intraluminal medical device having radiopacity comprising the steps of coextruding a stent preform comprised of a first metallic base material and a second metallic material, one of which has more radiopacity than the other. Preferably, the second material is more radiopaque than the first. The preform is coextruded in such a way that the second material is located at specified periodic intervals in the base material and forms a substantially smooth surface with the first base material. The preform may be extruded in the form of a sheet or tube. A strut pattern may then be formed in the stent preform.

DETAILED DESCRIPTIONS OF THE PREFERRED EMBODIMENTS

Figure 1:
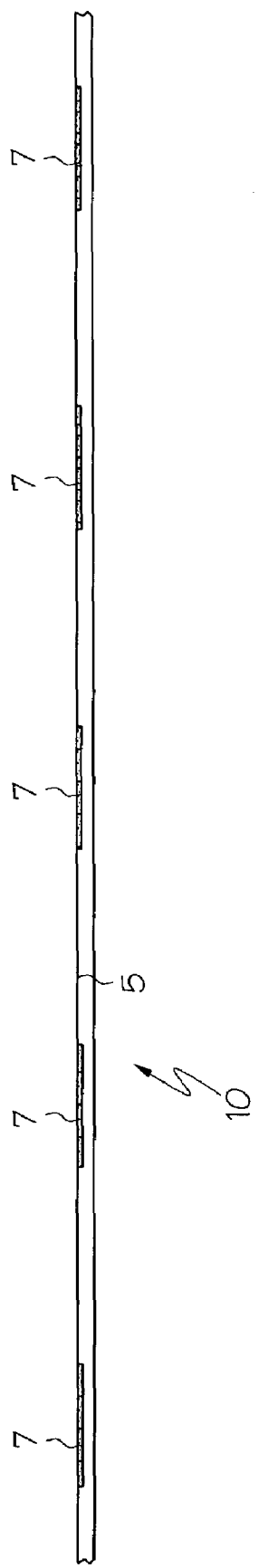
FIG. 1 is a side elevational view of a stent preform in a sheet form having the inlays as described by the present invention.

The present invention provides a radiopaque marker that may be conveniently, consistently and precisely affixed to intraluminal devices, in particular stents, that does not limit the expansion capabilities of expandable stents, and that has an acceptable, very low profile. The present invention also provides a convenient means for affixing such markers to the intraluminal devices of the present invention.

The radiopaque markers of the present invention may be utilized with any intraluminal devices, and in particular with stents, having various geometric shapes and materials. In addition, the radiopaque markers may be positioned anywhere on a stent. These markers allow an operator to easily view the stents using fluoroscopy to effectively identify the position, orientation, configuration, diameter and length of a stent within a blood vessel without obscuring a lesion or blood vessel being repaired, Generally, the intraluminal devices, or stents useful herein include tubular, flexible, expandable vascular or endoluminal stents adapted for deployment in a vessel or tract of a patient to maintain an open lumen. The stents are typically radially expandable stents formed from either a hollow tube or a sheet which may be polymeric, biocompatible metal, or metal-like materials with metal or metal-like materials being preferred.

Some preferred types of materials include metals or metal alloys including stainless steel, and shape memory alloys such as NITINOL® which is a nickel-titanium alloy.

Nitinol is discussed in U.S. Pat. No. 6,059,810 herein incorporated by reference in its entirety. This patent refers to an article by L. McDonald Schetky for a discussion of such alloys entitled "Shape-Memory Alloys" at pp 74-82 of Volume 241 (5) November 1979, SCIENTIFIC AMERICAN, and to "A Source Manual For Information On Nitinol and Ni Ti", first revision, by David Goldstein, Research and Technology Department, Feb. 1, 1980, Naval Surface Weapons Center, Dalgren, Va. 22448 (NSWC TR 80-59), both of which are incorporated by reference herein.

Other alloys useful for stent formation, in addition to Nitinol, are discussed in U.S. Pat. No. 5,725,570 herein incorporated by reference. This discussion includes stainless steel, as well as other superelastic materials including, e.g., silver-cadmium (Ag—Cd), gold-Cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron-beryllium ($Fe_3$—Be), iron-platinum ($Fe_3$—Pt), indium-thallium (In—Tl), iron-manganese (Fe—Mn), nickel-titanium-vanadium (Ni—Ti—V), iron-nickel-titanium-cobalt (Fe—Ni—Ti—Co), and copper-tin (Cu—Sn).

See also Schetsky, L. McDonald, "Shape Memory Alloys", Encyclopedia of Chemical Technology (3rd ed.), John Wiley & Sons, 1982, vol. 20. pp. 726-736 for a full discussion of superelastic alloys, herein incorporated by reference.

Some examples of radial expandable stents useful herein are described generally in application Ser. Nos. 08/511,076; 09/111,531; and 09/197,276 all now pending, the entire contents of which are herein incorporated by reference. Other radial expandable stents are described generally in U.S. Pat. No. 5,807,404, U.S. Pat. No 5,836,964 and U.S. Pat. No 5,922,005, the entire contents of which are herein incorporated by reference. Another useful stent configuration is described in U.S. Pat. No. 5,725,572 also incorporated by reference herein. The stents may either be self-expanding, or pressure-expandable.

The stents typically have a multitude of openings in the stent wall, and are open at both the proximal and the distal end. These openings in the stent wall are pattern etched into the sheet or tube. This can be accomplished by laser etching or cutting, by chemical etching, by metal stamping, and so forth. This etching, cutting or stamping process therefore creates the stent strut pattern.

The stents are fabricated having a predetermined inner diameter in a production state and are adapted for expansion to a larger diameter upon deployment in a vessel or tract.

The radiopaque marker bands may be formed of any radiopaque material, preferably a metal or metal alloy. Specific radiopaque materials useful herein include the noble metals such as gold, platinum, tantalum, rhenium and iridium, and the non-noble metal, silver. Radiopaque materials useful for providing stents with radiopacity are discussed in U.S. Pat. No. 5,725,570 herein incorporated by reference in its entirety. Some metals, such as tantalum, irradiate more brightly than others and the metal can therefore be selected on such basis. Some particular embodiments of the present invention utilize gold as the metal of choice. Gold is useful due to its nonallergenic qualities, as well as its radiopacity. Gold is known to produce less thrombus and tissue irritation.

As noted above, the radiopaque markers may be affixed anywhere on a stent. It is preferable that the markers are affixed at regular intervals. In particular embodiments, the radiopaque markers of the present invention are affixed at least to both a distal and a proximal end of a generally cylindrical stent. Other embodiments include affixing to a part of the body portion of the stent as well.

The present invention involves coextruding two materials, one of which has more radiopacity than the other, or one of the materials may be rolled, swaged or cold forged into the other material, resulting in inlays one material in another. Preferably, the more radiopaque material will be inlaid in a base material. For instance, gold may be inlaid in stainless steel. Using the latter technique of swaging, the radiopaque material may be uniformly forced or compressed into the base material of the stent. The radiopaque material is substantially flush with, or forms a substantially smooth surface with the base material of the stent.

Once the sheet having one material embedded in another, preferably the radiopaque material in the base material, has been formed, the strut pattern can be then be formed into the sheet by laser cutting, chemical etching or metal stamping, for instance. The sheet can then be rolled into a tubular form to join the edges which are then welded together to retain the tubular shape.

Alternatively, a stent preform in tubular form can be utilized, and the inlays can be rolled or swaged into the tubular form, or the two material may be coextruded together in tubular form. The strut pattern may then be formed in the tube.

The inlays may be set in a base material in such a way that they run circumferentially around the tubular member, parallel with the longitudinal axis, or they may run in a diagonal or spiral direction.

FIG. 1 illustrates generally at 10 a stent preform in the form of a sheet comprised of a first base material 5. Inlays of a second material 7 more radiopaque than the first material 5 are shown at relatively uniform intervals across the sheet. Alternatively, in FIG. 1, as well as in all the other figures shown below, the more radiopaque material can be used as the base material and the less radiopaque material inlaid into it.

Figure 2:
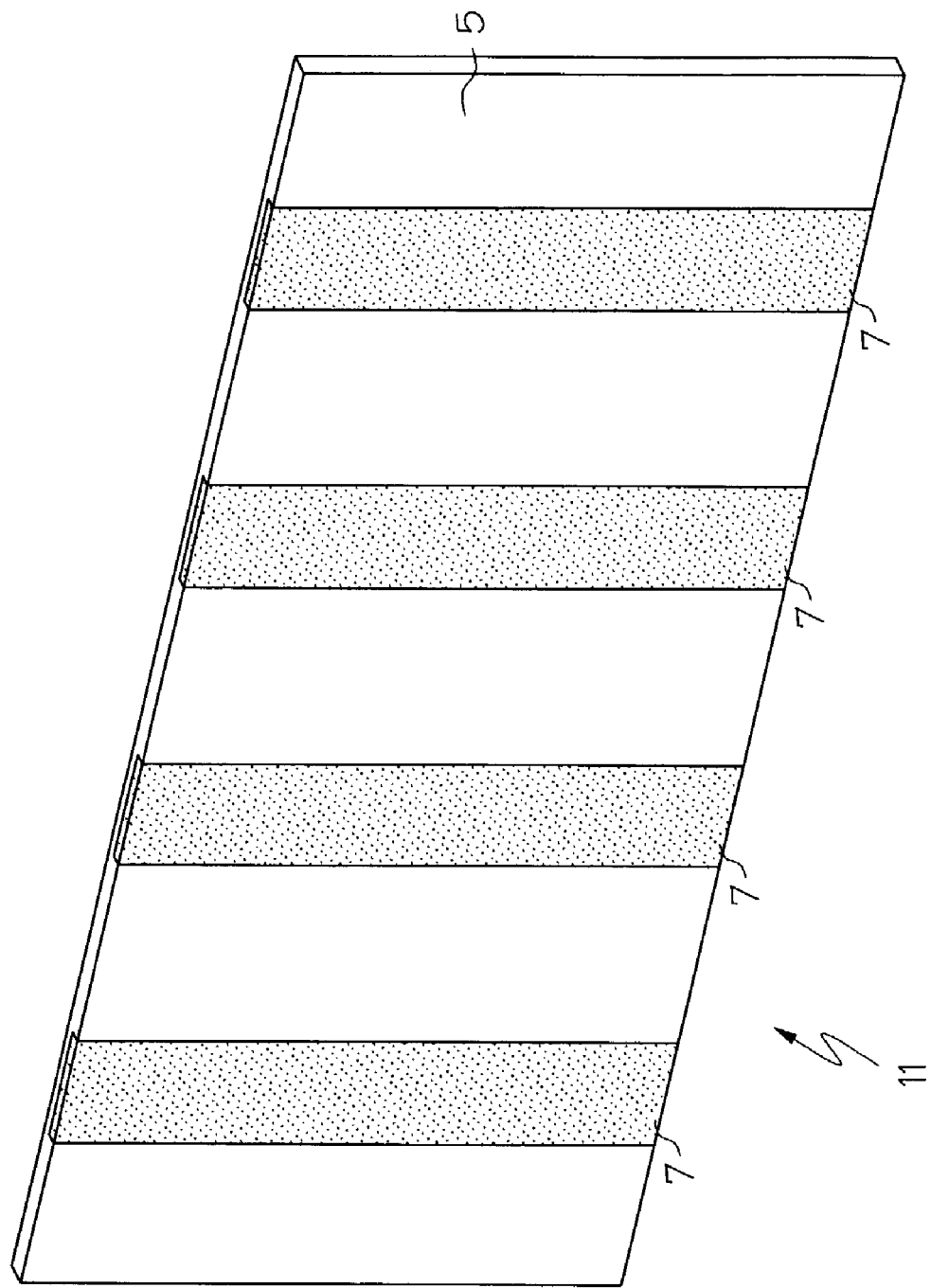
FIG. 2 is a flat view of a stent preform in sheet form having inlays as described by the present invention.

FIG. 2 illustrates generally at 11, a different view of a stent preform in the form of a sheet comprised of a first base material 5. The inlays 7 formed of the second more radiopaque material are shown at relatively uniform intervals across the sheet. FIGS. 1 and 2 are intended to be representative of what an inlaid pattern may look like when the stent preform is in the form of a sheet, but are in no way intended to limit the scope of the invention. The number of inlays can be infinitely varied, as can the patterns with which the inlays are presented in the stent preform.

Figure 3:
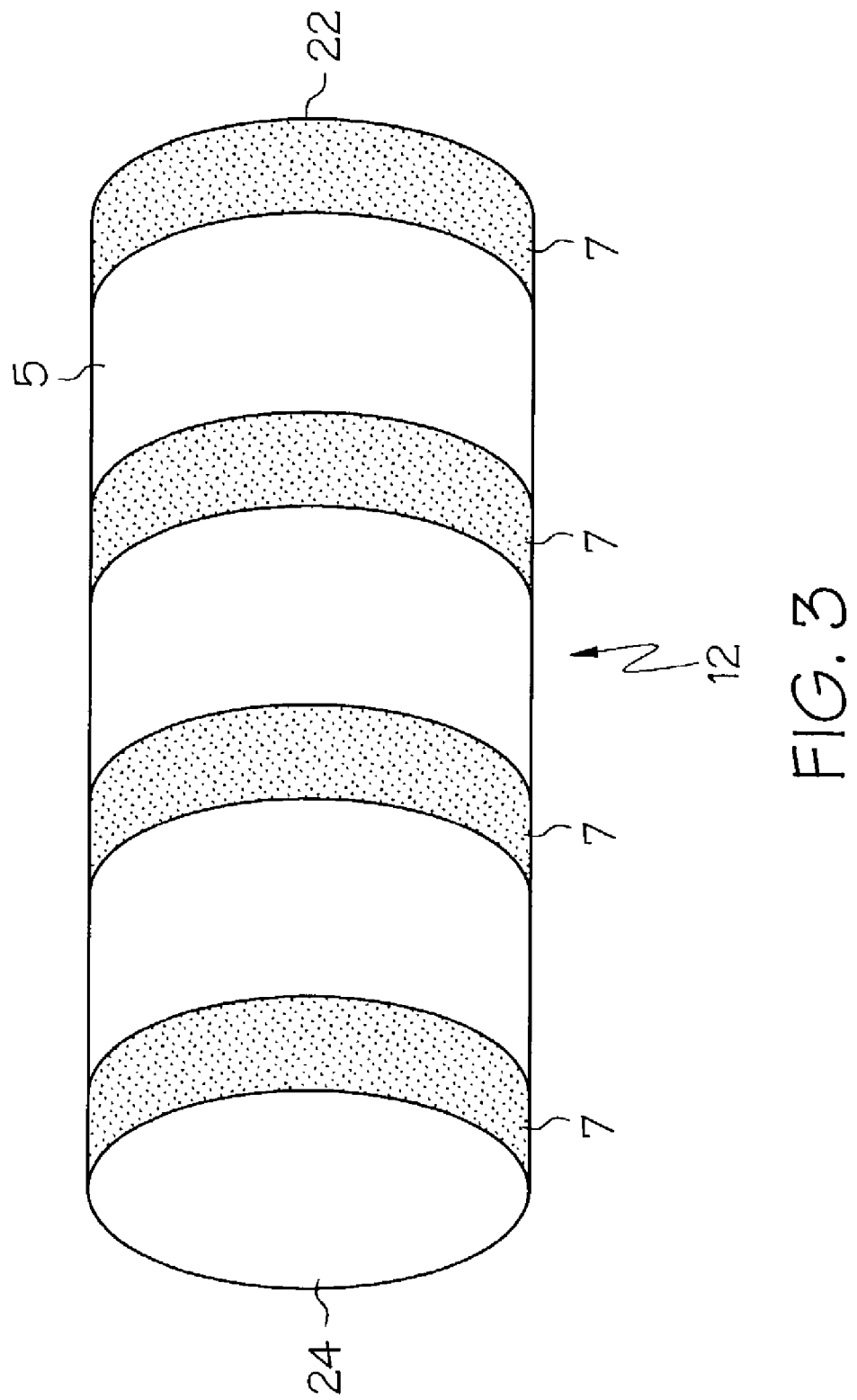
FIG. 3 is a side view of a stent in tubular form having the inlays running around the circumference of the tubular form.

FIG. 3 illustrates generally at 12, a stent preform in tubular form. The tubular form has a distal end 22 and a proximal end 24. The tubular preform is formed of a first base material 5. The inlays 7, are formed of a second material more radiopaque than the first. The first and second material may comprise one material, or may comprise a combination or alloy of two or more different materials. The inlays 7 are shown running around the circumference of the tubular preform 12. Strut patterns have not yet been formed in this tubular preform.

Figure 4:
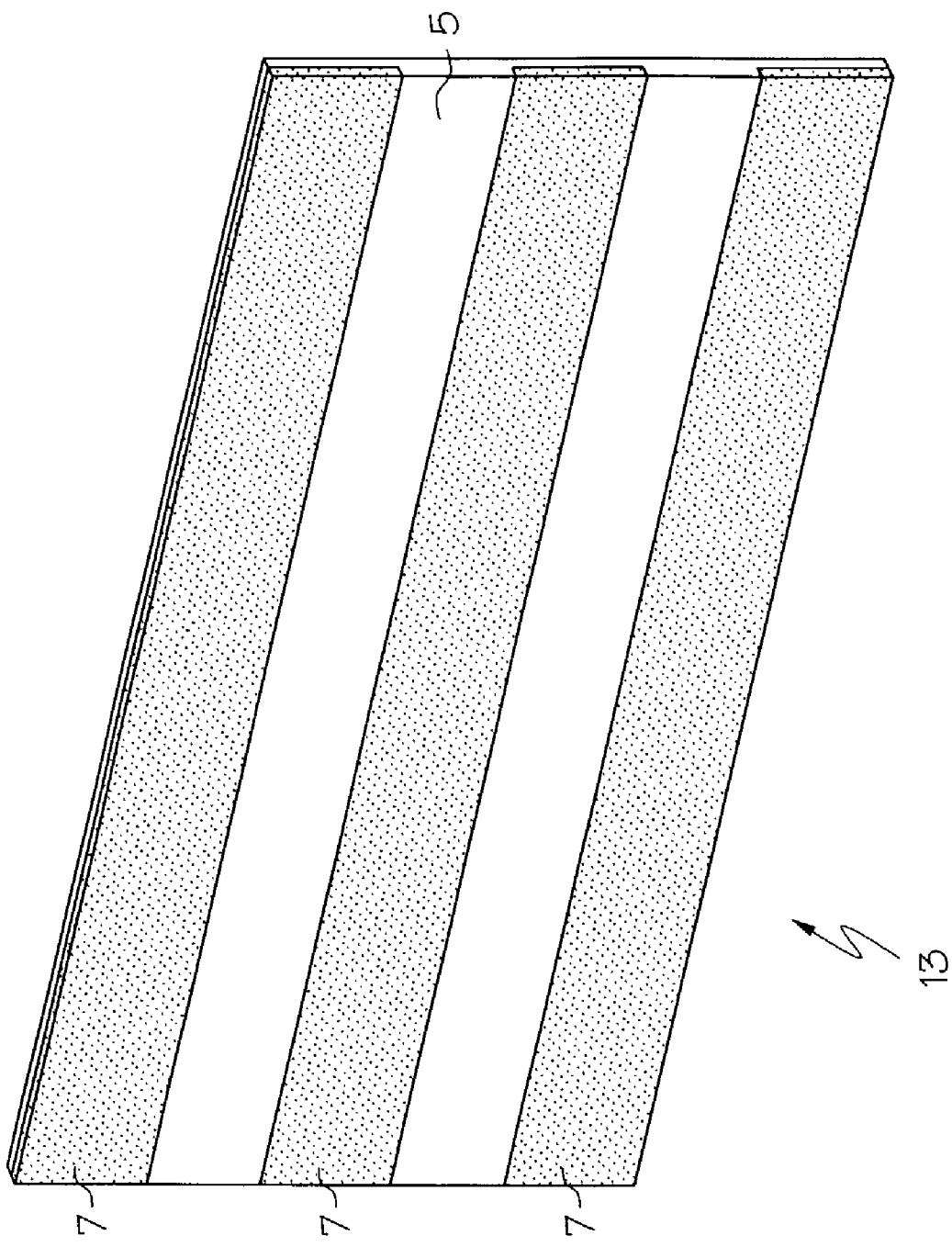
FIG. 4 is a flat view of a stent preform in sheet form wherein the inlays run in a longitudinal direction.

FIG. 4 illustrates generally at 13, a stent preform in sheet form formed of a first base material 5. The inlays 7 are formed of a more radiopaque material than the base material 5. The inlays 7 are shown to run in a longitudinal direction.

Figure 5:
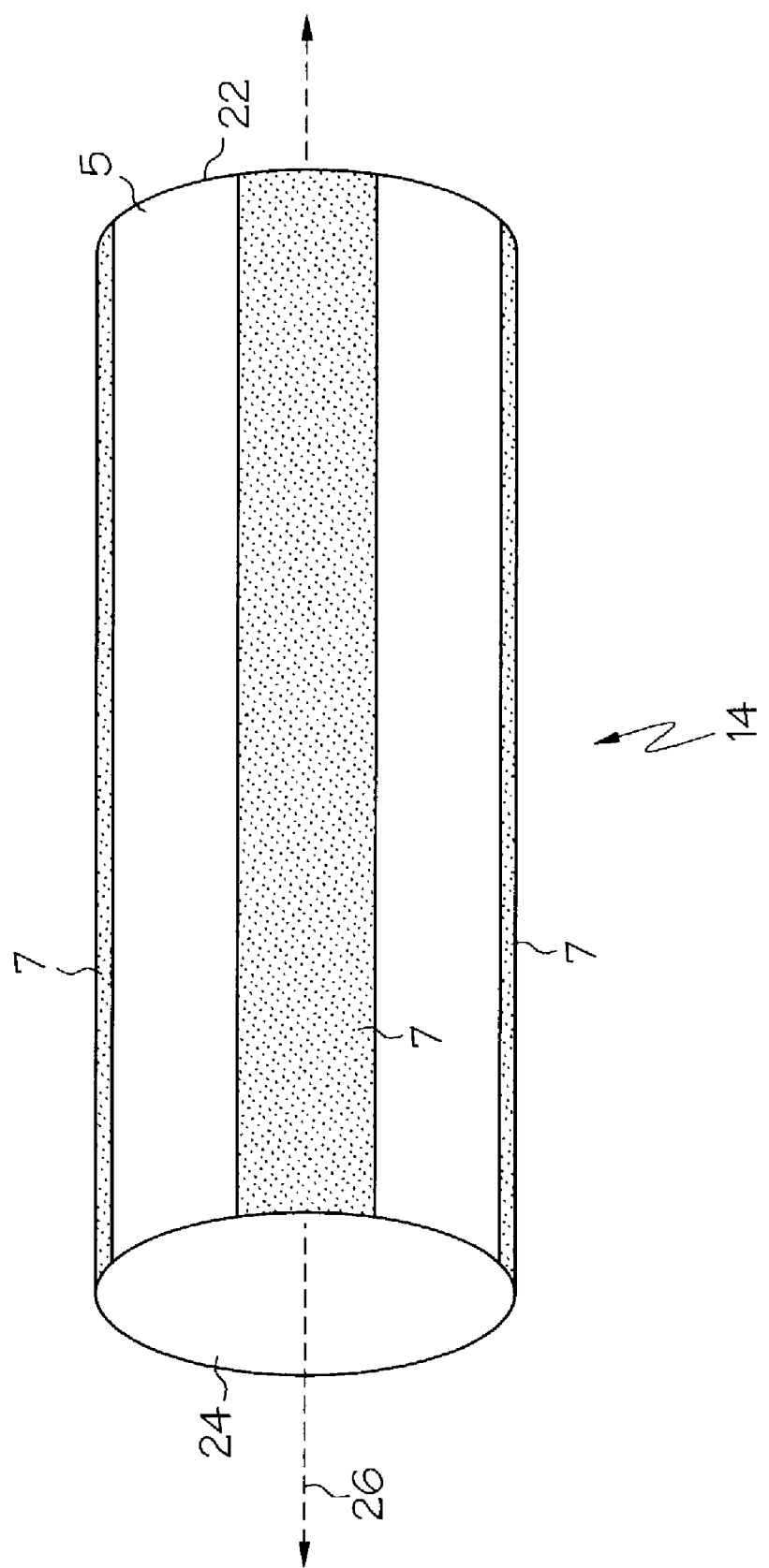
FIG. 5 shows a side elevational view of a stent preform in tubular form having a similar inlaid pattern as that shown in FIG. 4 wherein the inlays run with the longitudinal axis of the tubular preform.

FIG. 5 illustrates generally at 14, a stent preform in tubular form having a distal end 22, and a proximal end 24. The tubular preform is formed of a first base material 5 and inlaid in the base material is a second more radiopaque material 7. The inlays 7 run with the imaginary longitudinal axis 26 of the tubular preform 14.

Figure 6:
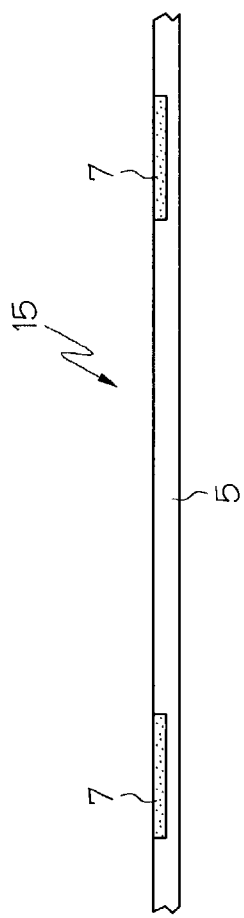
FIG. 6 is a side elevational view of a stent preform in sheet form wherein the inlays are at the distal and proximal ends of the preform.
Figure 7:
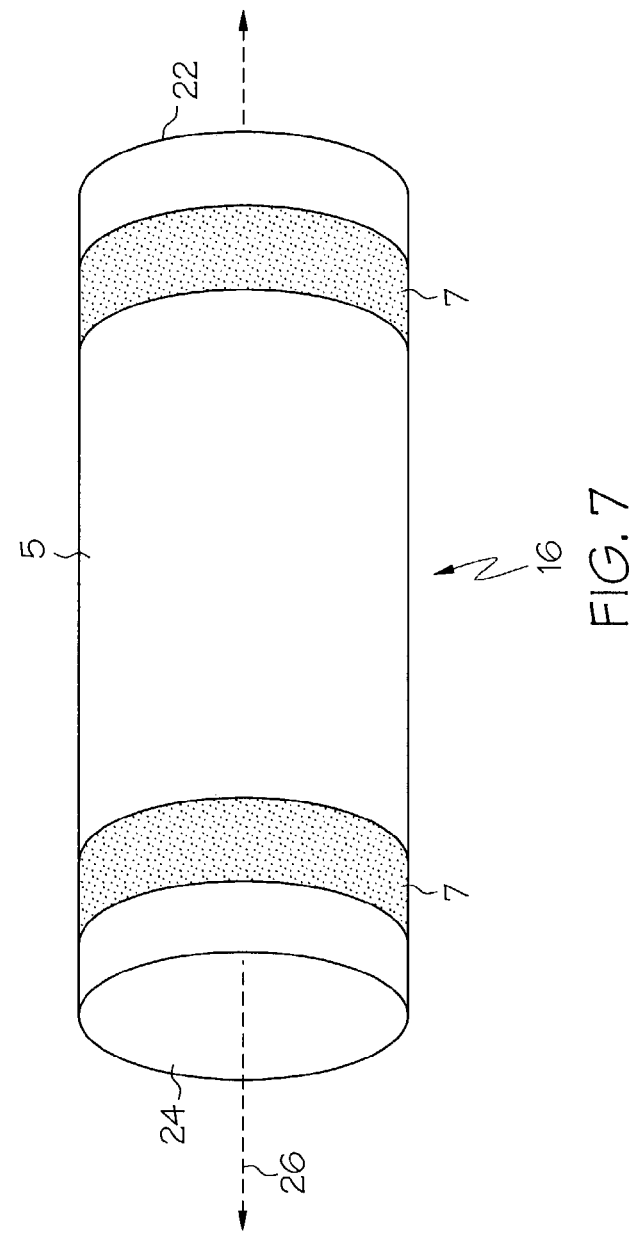
FIG. 7 is a side view of a stent preform in tubular form illustrating the same inlaid pattern as that shown in FIG. 6.

FIG. 6 illustrates generally 15 a side elevational view of a stent preform in the form of a sheet wherein there are only two radiopaque inlays 7 shown in the base material 5. Once in tubular form, shown in FIG. 7 generally at 16, the radiopaque inlays 7 will be at the distal 22 and proximal 24 ends of the stent preform. The inlays 7 run circumferentially around the stent preform 16.

Figure 8:
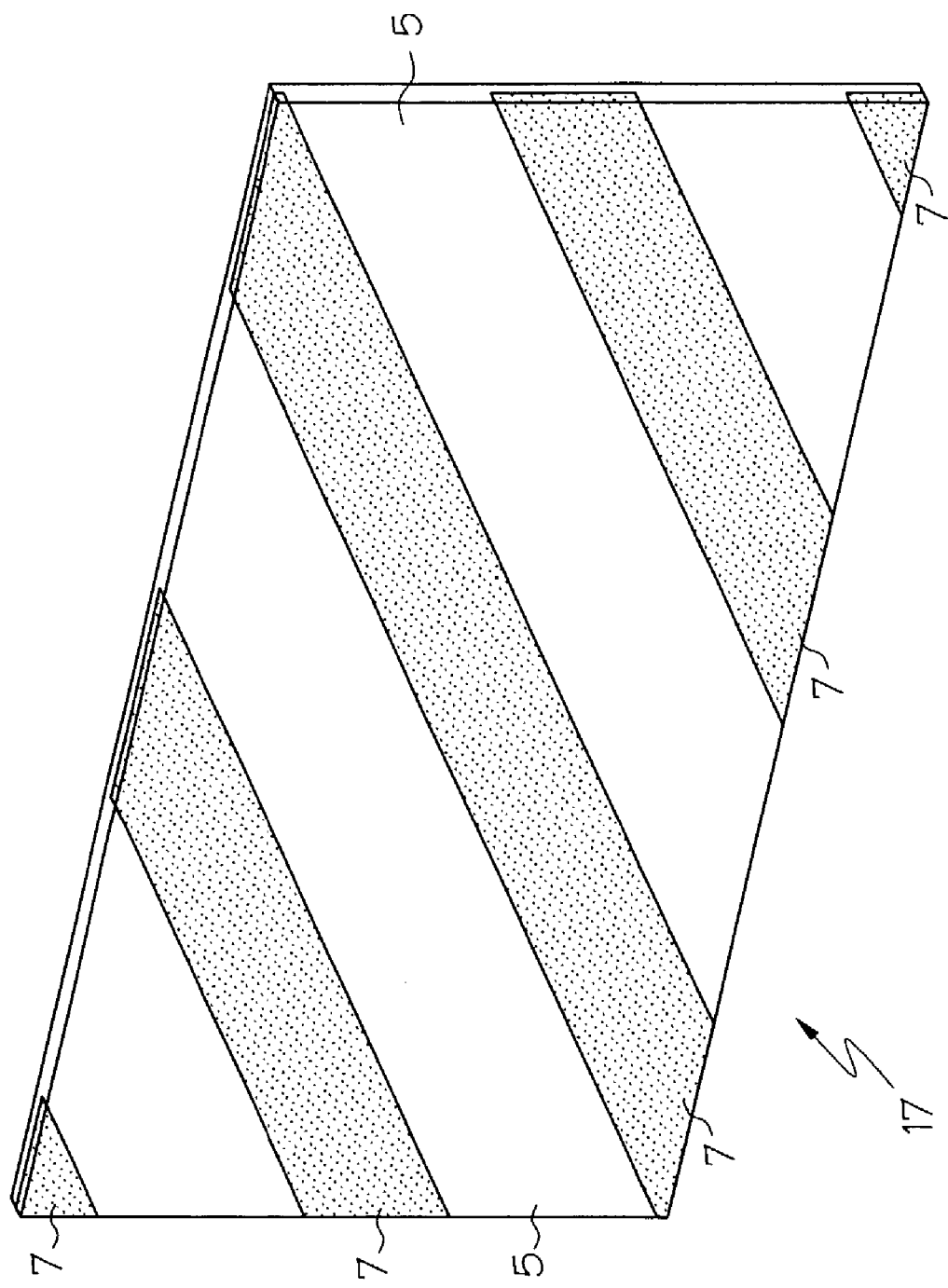
FIG. 8 is a flat view of a stent preform in sheet form wherein the inlays run in a diagonal direction.

FIG. 8 illustrates generally at 17, a flat view of a stent preform in the form of a sheet comprised of a first base material 5. The inlays 7 formed of the second more radiopaque material are shown at relatively uniform intervals in a diagonal pattern across the sheet.

Figure 9:
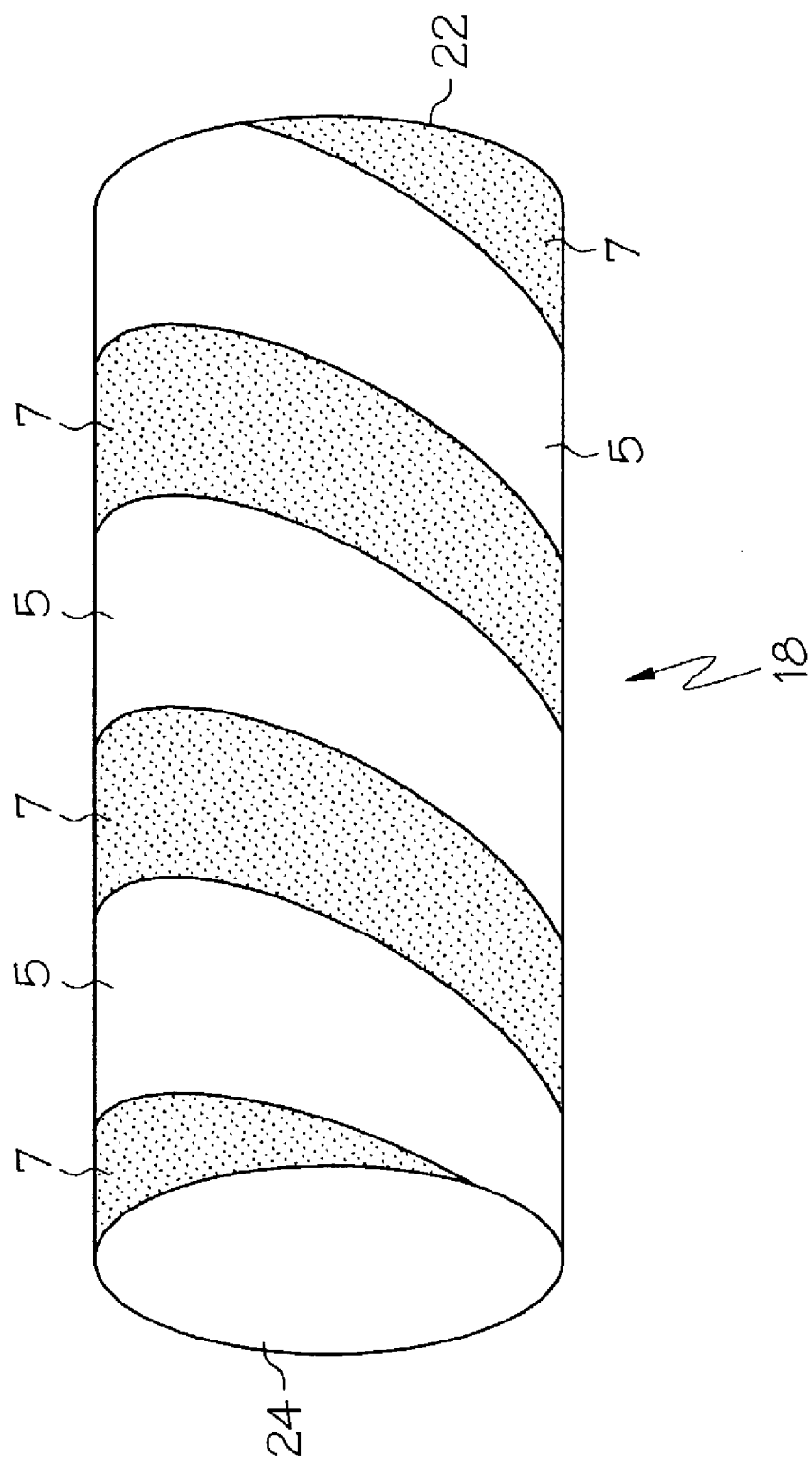
FIG. 9 is a side view of a stent preform in tubular form having a similar inlaid pattern as that shown in FIG. 8 wherein the inlays run in a diagonal direction.

FIG. 9 illustrates generally at 18, a stent preform in tubular form. The tubular form has a distal end 22 and a proximal end 24. The tubular preform is formed of a first base material 5. The inlays 7, are formed of a second material more radiopaque than the first and are shown in a diagonal pattern around the circumference of the tubular stent preform 18. The first and second material may comprise one material, or may comprise a combination or alloy of two or more different materials. Strut patterns have not yet been formed in this tubular preform. FIGS. 8 and 9 are intended to be representative of what an inlaid pattern may look like when the stent preform is in the form of a sheet, but are in no way intended to limit the scope of the invention. The number of inlays can be infinitely varied, as can the patterns with which the inlays are presented in the stent preform.

Figure 10:
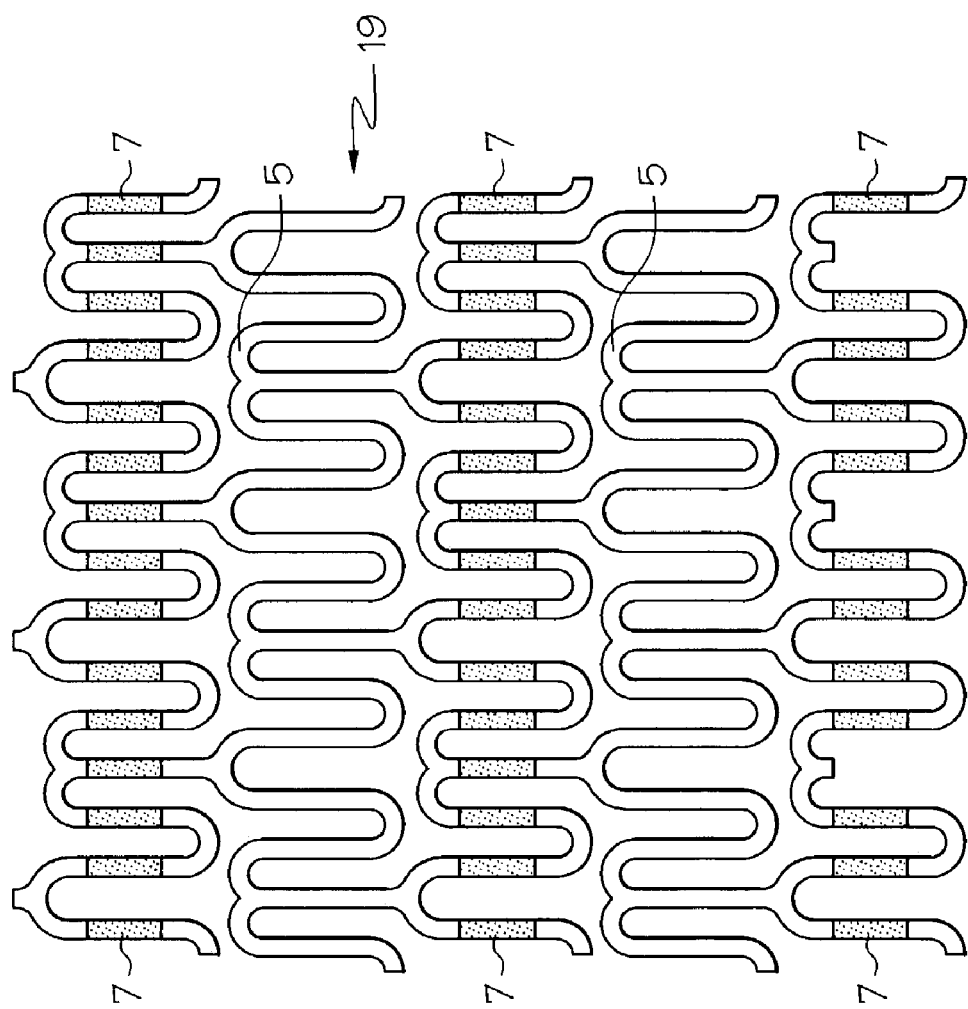
FIG. 10 is a partial view of a stent embodying the inlays of the present invention.

FIG. 10 illustrates generally at 19 a partial flat view of stent formed of a first base material 5 embodying the inlays 7 formed of a second material more radiopaque than the base material. When the same stent is shown in a tubular form, the inlays will run in a pattern around the circumference of the stent.

Figure 11:
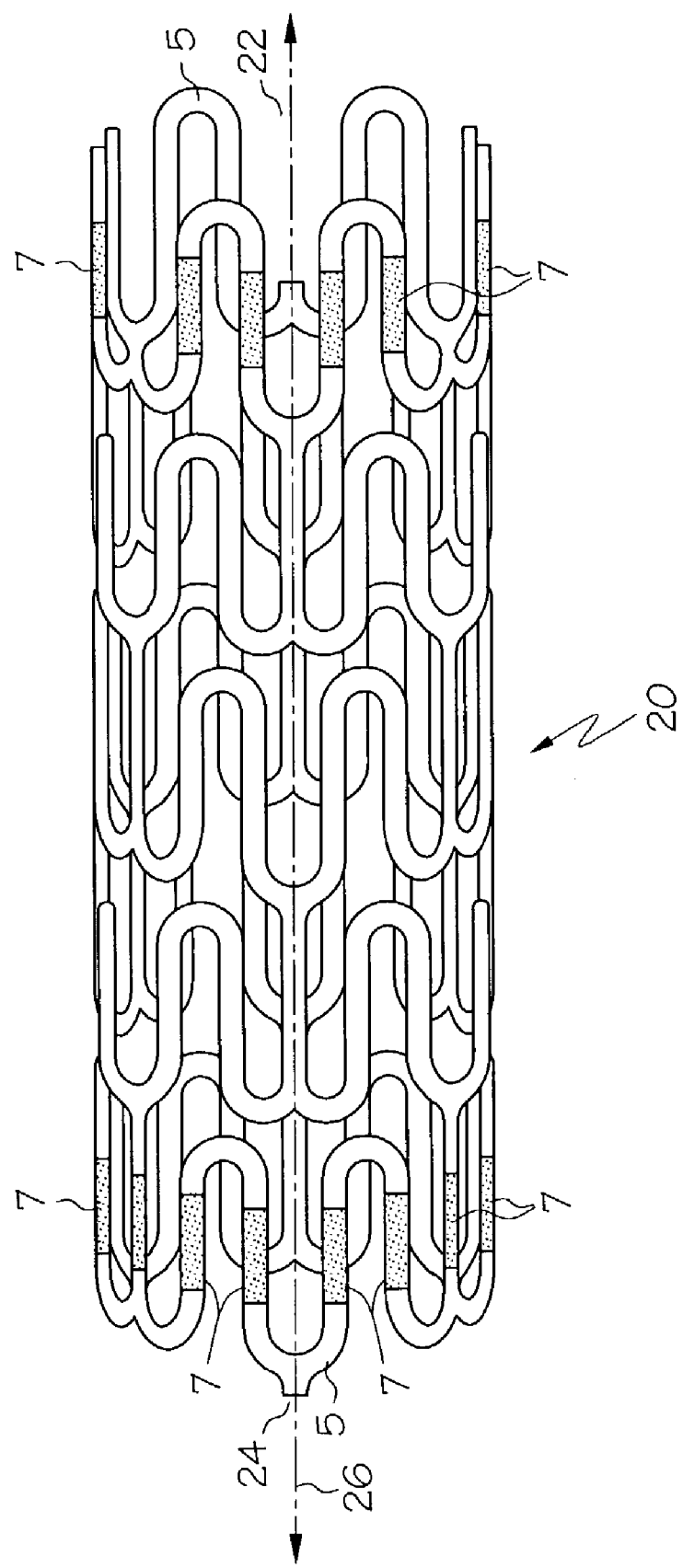
FIG. 11 shows a three-dimensional view of a stent in tubular form illustrating inlays at the distal and proximal end of the stent.

FIG. 11 illustrates generally at 20, a stent having the same type of strut pattern as shown in FIG. 10 formed of a first base material 5, and having radiopaque inlays 7, at the proximal 22 and distal ends 24 of the stent 18. Stent 18 may alternatively have various inlays at one or more intervals in the body portion, in particular, in the center portion, of the stent 18.

Stents of the type illustrated in FIGS. 10 and 11 are described in U.S. Pat. No. 5,725,572 incorporated by reference herein.

Figure 12:
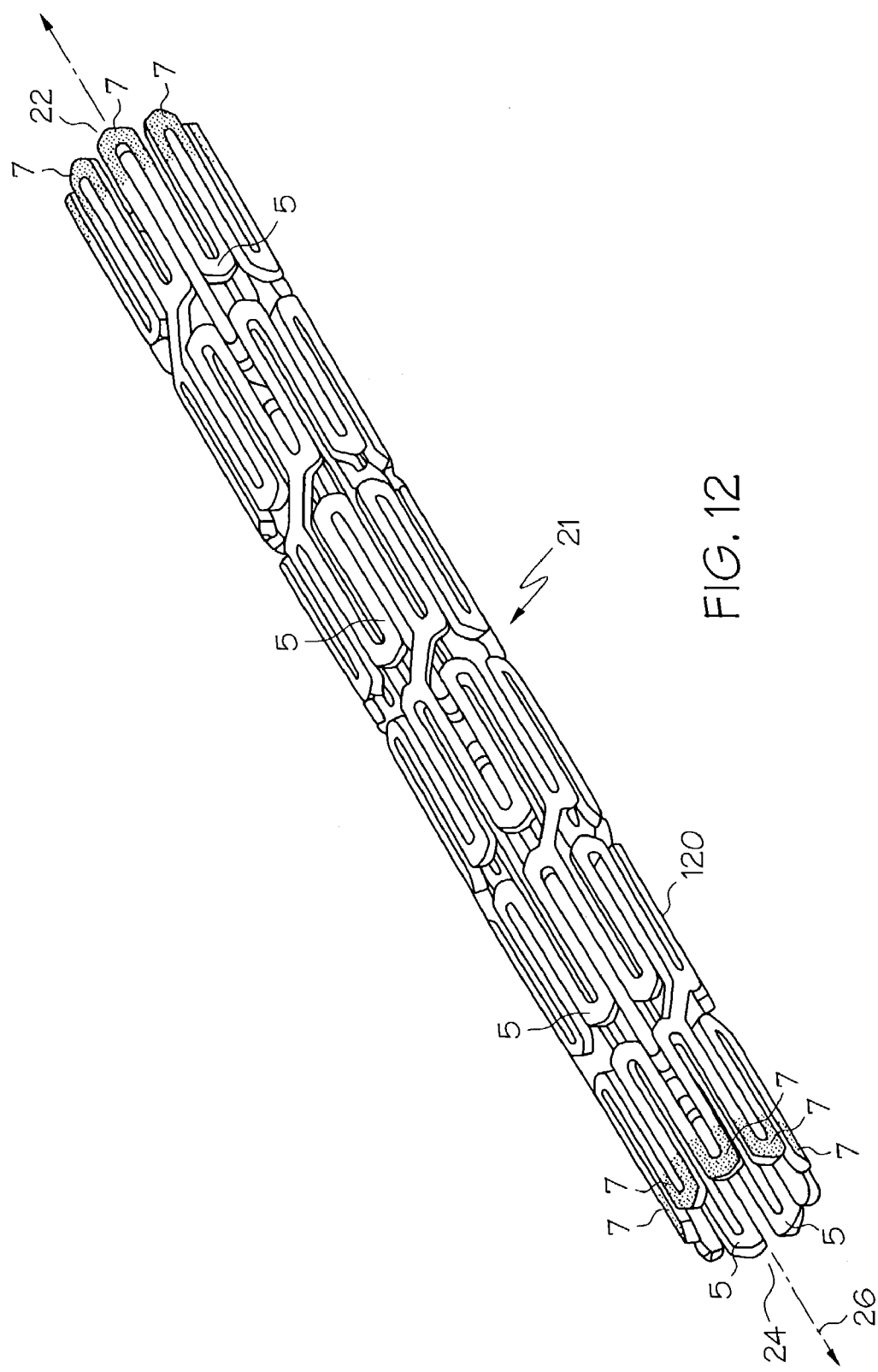
FIG. 12 shows a three-dimensional view of a different embodiment of a stent in tubular form having inlays at the proximal and distal ends.

FIG. 12 illustrates generally at 21, a radial expandable stent having a different strut pattern than that shown in FIG. 11. In all other respects, the stent embodies the same features of the present invention as shown in FIG. 10. Stents of this type are described in U.S. Pat. No. 5,807,404, U.S. Pat. No. 5,836,964 and U.S. Pat. No. 5,922,005 all of which are incorporated by reference herein in their entirety.

Figure 13:
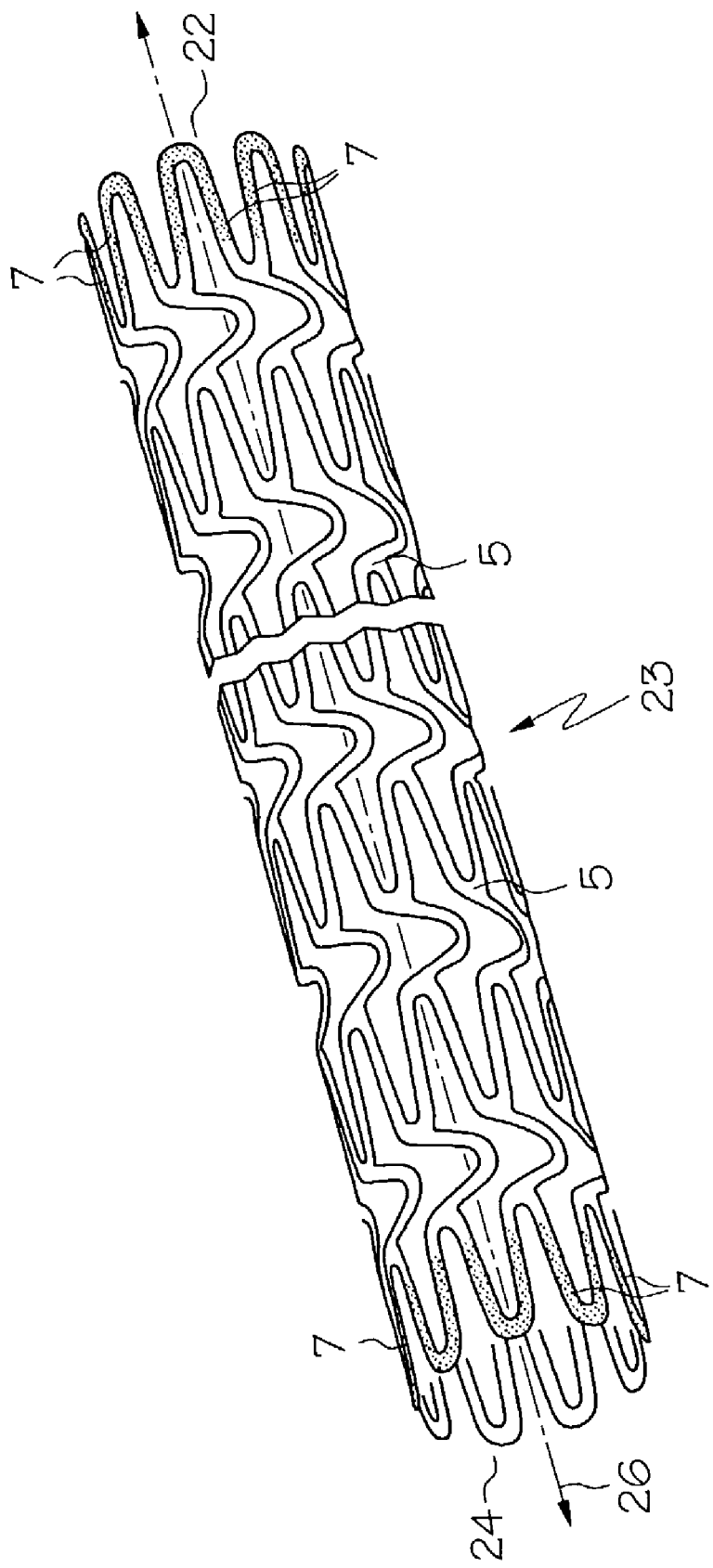
FIG. 13 shows a three-dimensional view of yet another embodiment of a stent in tubular form having inlays at the proximal and distal ends of the stent.

FIG. 13 illustrates generally at 23, a radial expandable stent having a different strut pattern than that shown in FIGS. 10-12. In all other respects, stent 20, embodies the same features of the present invention as shown in FIGS. 10-12. Stents of the type shown in FIG. 11 are described in U.S. patent application Ser. No. 08/511,076 incorporated by reference herein in its entirety.

Figure 14:
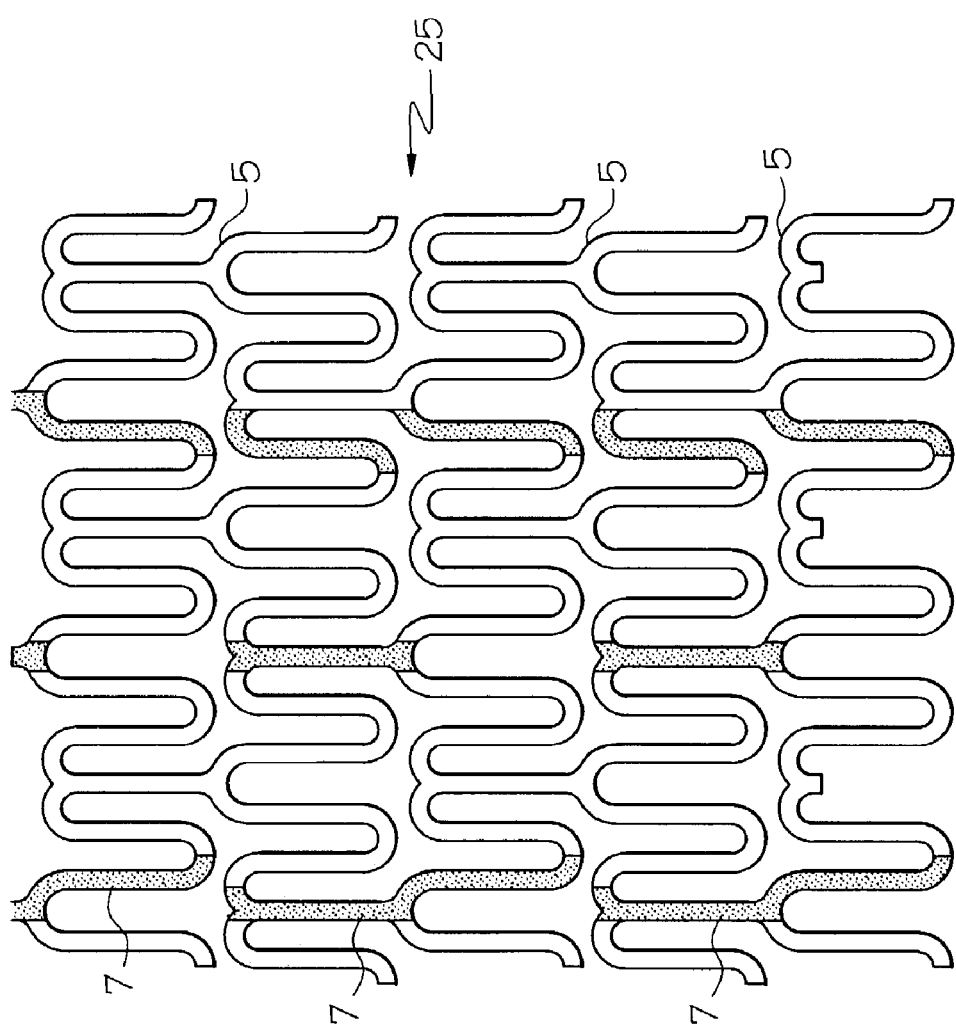
FIG. 14 is a partial view of a stent embodying the inlays of the present invention shown in a different pattern than FIG. 10.

FIG. 14 illustrates generally at 25, a partial flat view of stent formed of a first base material 5 embodying the inlays 7 formed of a second material more radiopaque than the base material. When the same stent is shown in tubular form, the inlays will be a pattern that runs with the longitudinal axis of the stent.

Figure 15:
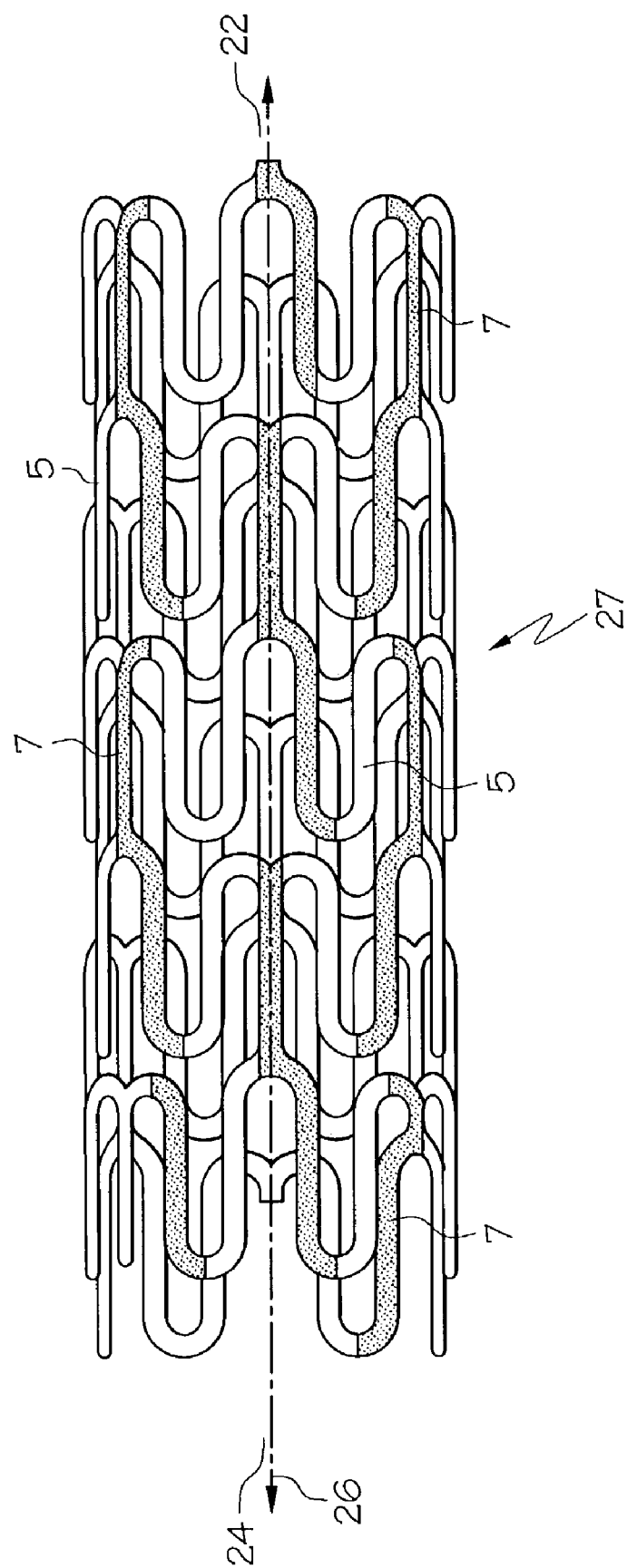
FIG. 15 shows a three-dimensional view of a stent in tubular form illustrating inlays running with the longitudinal axis of the stent.

FIG. 15 illustrates generally at 27, a stent having the same type of strut pattern as shown in FIG. 14 formed of a first base material 5, and having radiopaque inlays 7 are shown in a pattern that runs with the longitudinal axis 26 of the stent.

Figure 16:
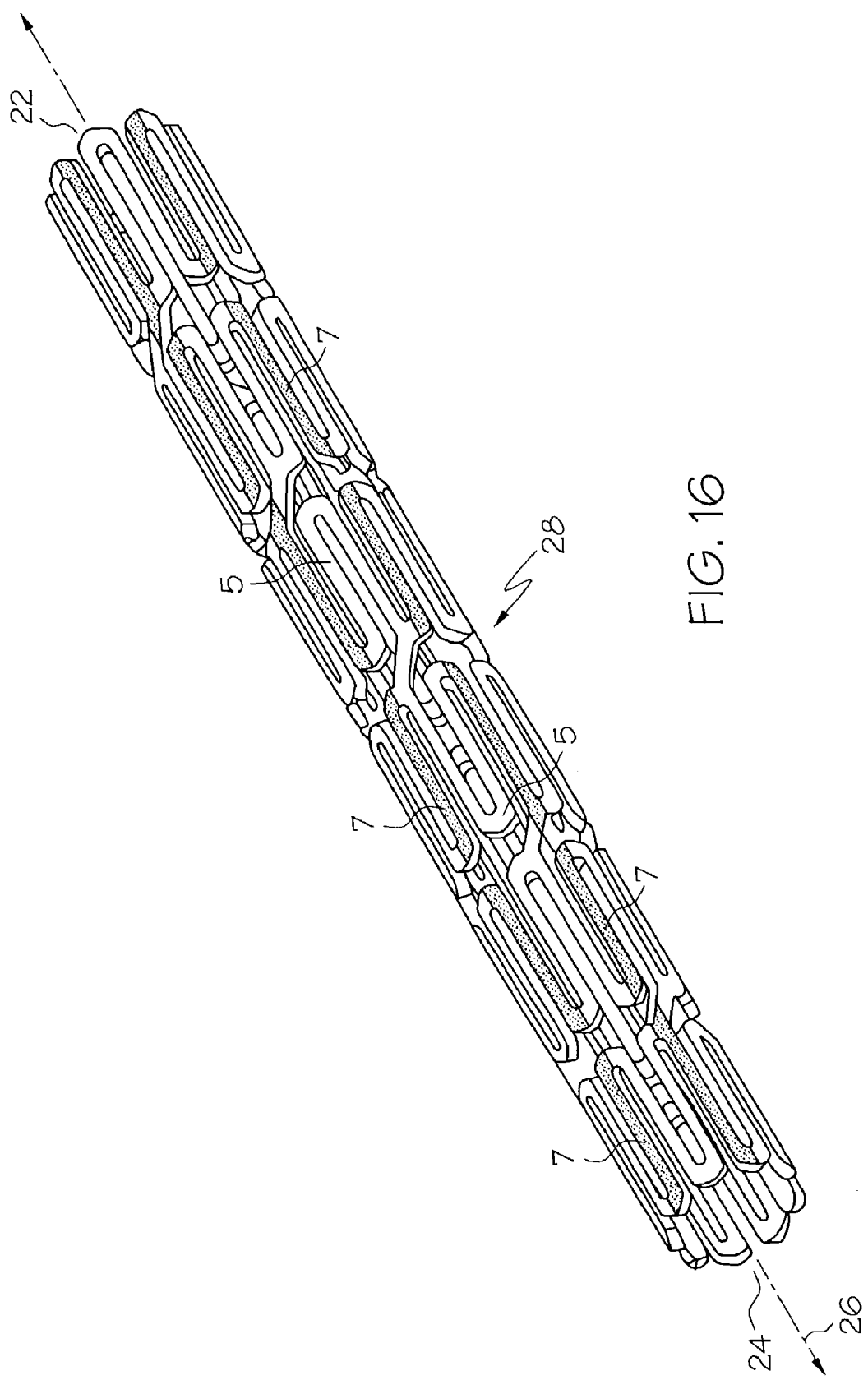
FIG. 16 illustrates a different embodiment of a stent in tubular form having inlays running with the longitudinal axis of the stent.

FIG. 16 illustrates generally at 28, a radial expandable tubular stent having a different strut pattern than that shown in FIG. 15. In all other respects, the stent embodies the same features of the present invention as shown in FIG. 15. The inlays 7 run parallel to the longitudinal axis 26 of the stent.

Figure 17:
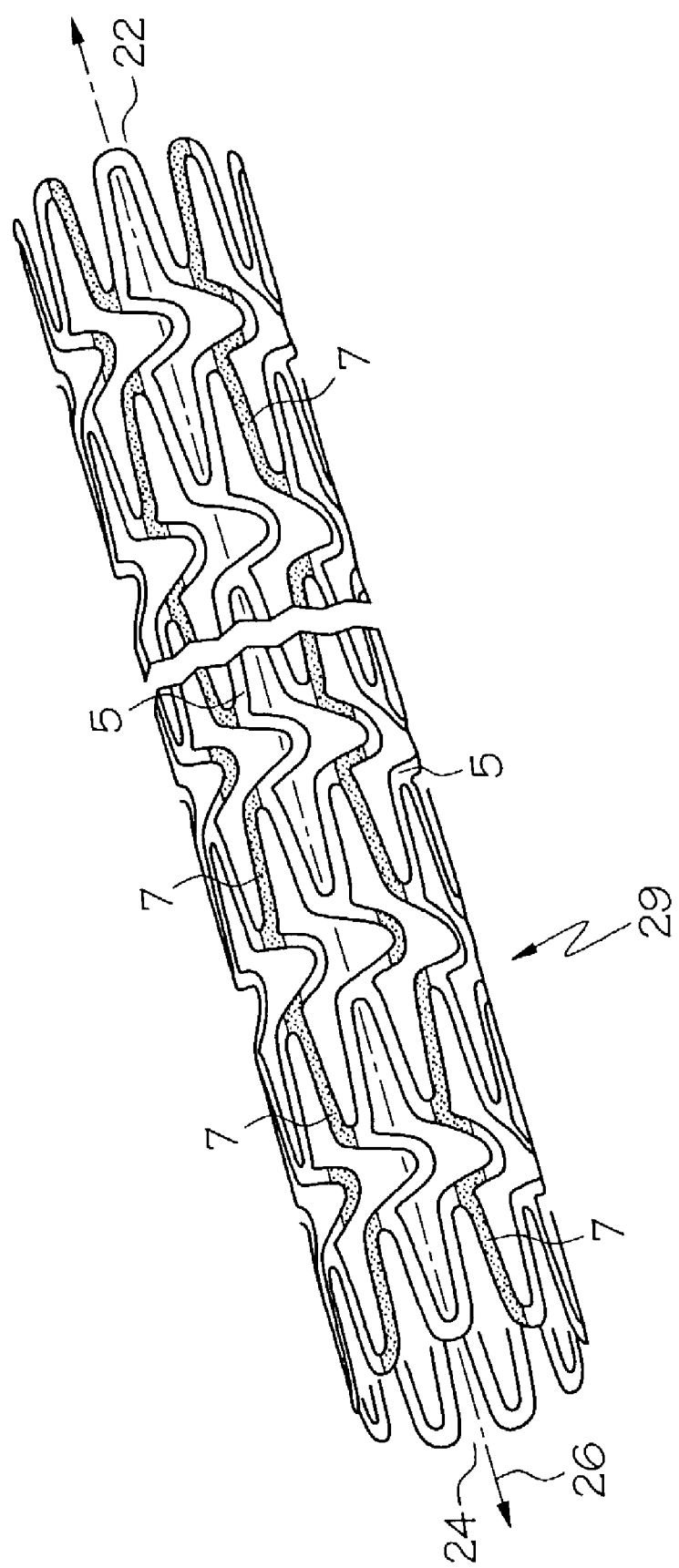
FIG. 17 illustrates yet a different embodiment of a stent in tubular form having inlays running with the longitudinal axis of the stent.

FIG. 17 illustrates generally at 29, a radial expandable tubular stent having yet a different strut pattern than the stents illustrated in FIGS. 15 or 16. In all other respects the stent embodies the same features of the present invention as shown in FIGS. 15 and 16. The inlays run parallel to the longitudinal axis 26 of the stent.

FIGS. 18-21 show the same stents as FIGS. 14-17 consecutively except that the inlays 7 are shown in a diagonal pattern across the stent.

Figure 18:
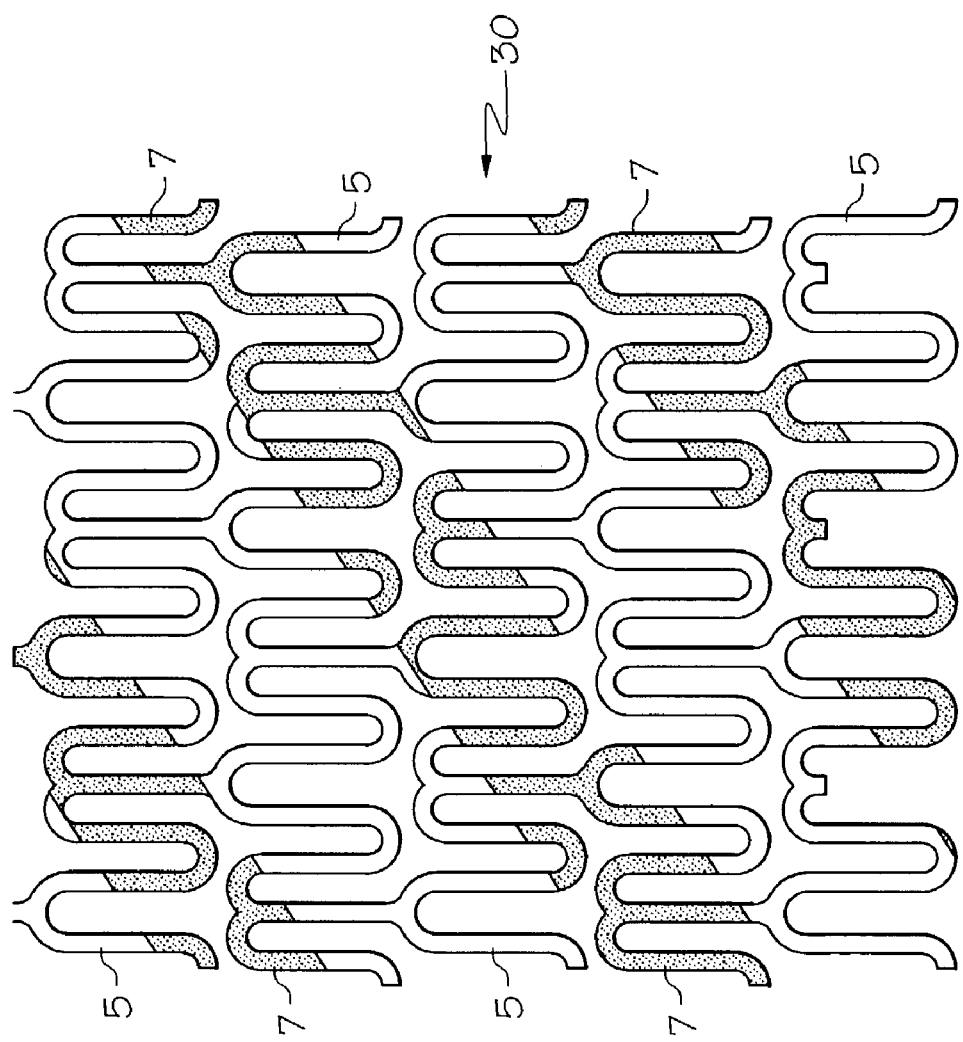
FIG. 18 is a partial view of a stent embodying the inlays of the present invention shown in a different pattern than those of FIGS. 10 and 14.

FIG. 18 illustrates generally at 30, a partial flat view of stent formed of a first base material 5 embodying the inlays 7 formed of a second material more radiopaque than the base material. When the same stent is shown in tubular form, the inlays will be a pattern that runs diagonally across the stent, and around the circumference.

Figure 19:
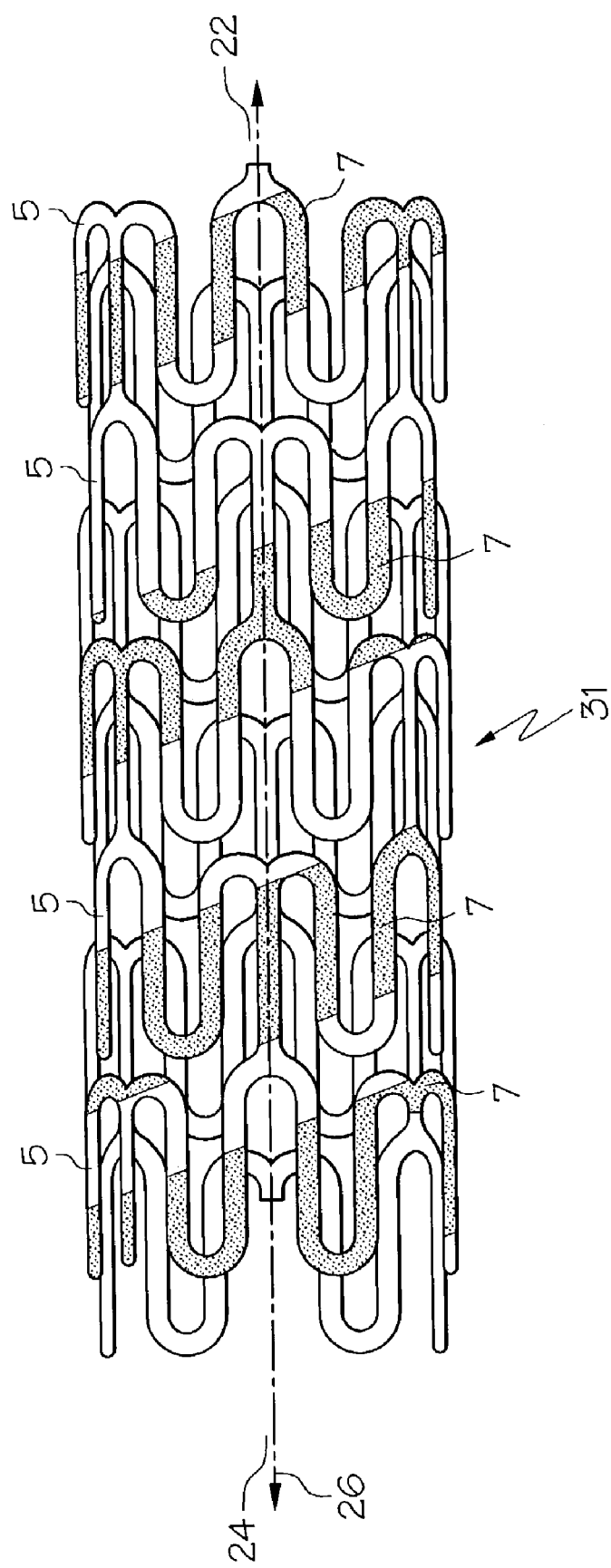
FIG. 19 shows a three-dimensional view of a stent in tubular form illustrating inlays in a diagonal pattern across the stent.

FIG. 19 illustrates generally at 31, a stent having the same type of strut pattern as shown in FIG. 18. The stent 31 is formed of a first base material 5, and having inlays 7 shown in a pattern that runs diagonally across the stent and around the circumference of the stent 31. Preferably the inlays are formed of a material that is more radiopaque than the base material.

Figure 20:
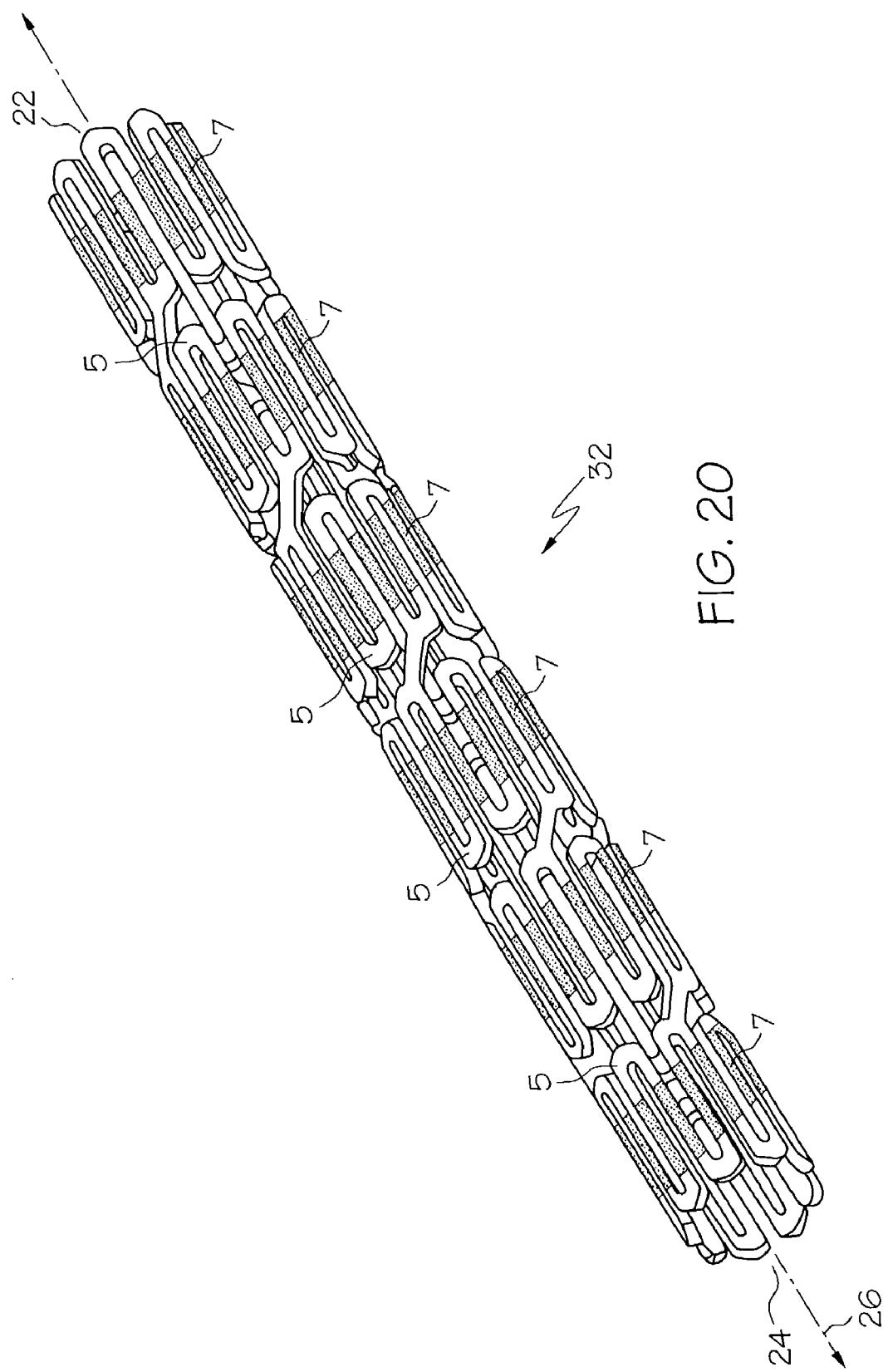
FIG. 20 shows a three-dimensional view of a different embodiment of a stent in tubular form having inlays running in a diagonal pattern across the stent.

FIG. 20 illustrates generally at 32, a radial expandable tubular stent having a different strut pattern than that shown in FIG. 19. In all other respects, the stent embodies the same features of the present invention as shown in FIG. 19. The inlays 7 run diagonally across the stent 32 and around the circumference of the stent 32.

Figure 21:
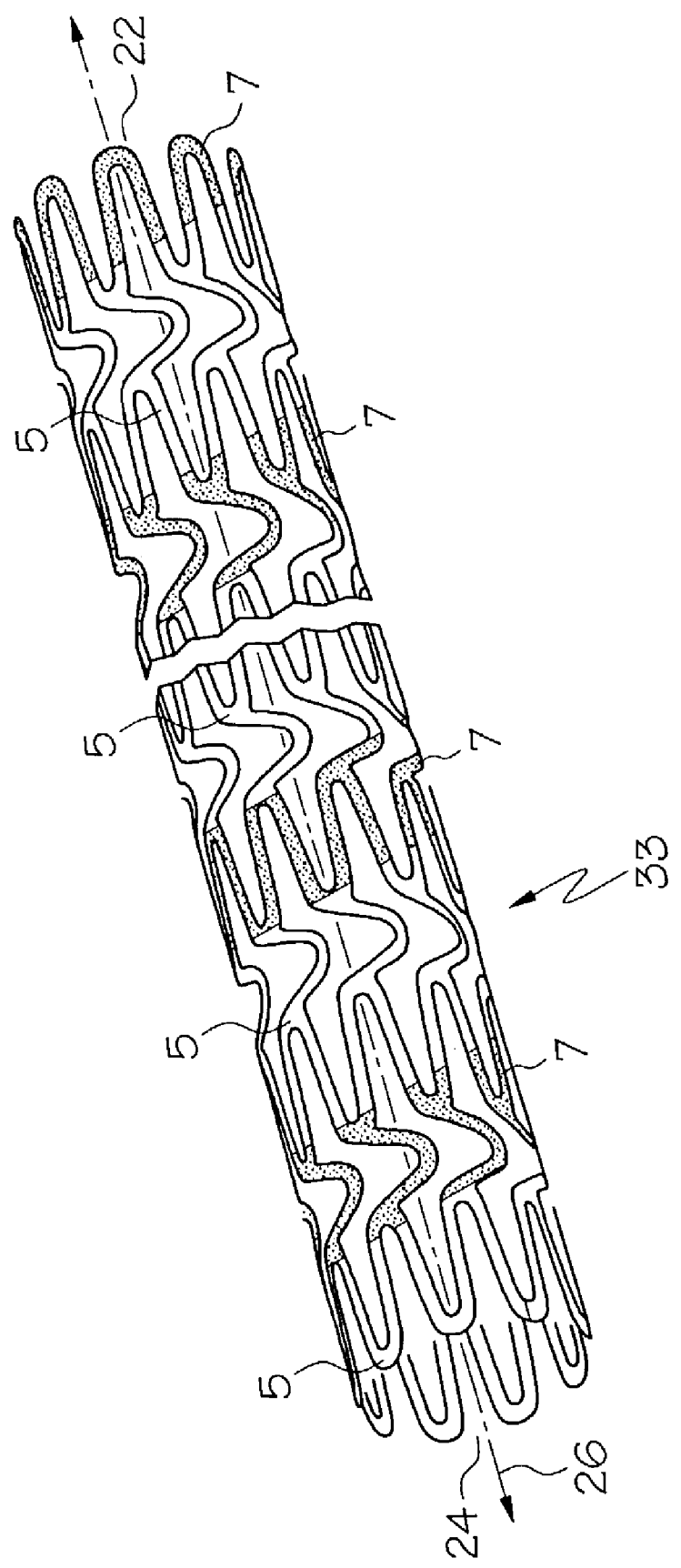
FIG. 21 shows a three-dimensional view of yet a different embodiment of a stent in tubular form having inlays running in a diagonal pattern across the stent.

FIG. 21 illustrates generally at 33, a radial expandable tubular stent having yet a different strut pattern than the stents illustrated in FIGS. 19 or 20. In all other respects the stent embodies the same features of the present invention as shown in FIGS. 19 and 20. The inlays run diagonally across the stent 33 and around the circumference of the stent 33.

Any of the stents illustrated in FIGS. 10-21 may also have other inlaid patterns. Those shown are for illustrative purposes only, and are not intended as a limitation on the scope of the invention. The second material may be inlaid in the first base material in any pattern desirable. The present invention may therefore be utilized to form any radiopaque pattern in a stent, and not just those patterns exemplified above.

Preferably, the second, inlaid material is more radiopaque than the first base material, but, if so desired, the more radiopaque material may be utilized as the base, and the less radiopaque material may be inlaid in the more radiopaque material. However, the latter may be less economically efficient if the more radiopaque material is a noble metal, for instance, and the first material is stainless steel.

It can be seen that this formation of a radiopaque marker or markers in the stent can be accomplished without interfering with the mechanical properties of the stent itself. The method allows for the radiopaque material to be captured securely within the the base material of the stent so that a robust mechanical type of bond is formed and the radiopaque inlays will not accidentally disengage. Thus, it can be seen that it is possible to easily provide a plurality of radiopaque markers in a stent in a feasible and economic manner.

With the radiopaque marker elements in place attached to the ends of the stent, the location and orientation of the stent can be precisely determined both before, during and after implantation and radial expansion of the surgical stent within the body lumen.

The invention claimed is:

1. A method of forming an intraluminal medical device having radiopacity comprising the steps of:
   a) coextruding a stent preform said preform being comprised of a first metallic base material and a second metallic material wherein one of said first material and said second material is more radiopaque than the other, said second material being located at specified periodic intervals in said base material and said second material forming a substantially smooth surface with said first base material in said stent preform;
   b) forming a strut pattern in said stent preform.

2. The method of claim 1 wherein said second material is more radiopaque than said first material.

3. The method of claim 1 wherein said stent preform is coextruded in the form of a sheet or a tube.

* * * * *